(12) United States Patent
Glaser et al.

(10) Patent No.: US 11,659,861 B2
(45) Date of Patent: May 30, 2023

(54) DUAL PRODUCT VAPORIZER METHOD AND DEVICES

(71) Applicants: Emma S. Glaser, Charlottesville, VA (US); Judith Cotton, Charlottesville, VA (US)

(72) Inventors: Emma S. Glaser, Charlottesville, VA (US); Judith Cotton, Charlottesville, VA (US)

(*) Notice: Subject to any disclaimer, the term of this patent is extended or adjusted under 35 U.S.C. 154(b) by 0 days.

(21) Appl. No.: 17/670,517

(22) Filed: Feb. 14, 2022

(65) Prior Publication Data

US 2022/0160032 A1 May 26, 2022

Related U.S. Application Data

(63) Continuation of application No. 17/149,749, filed on Jan. 15, 2021, now Pat. No. 11,259,565.

(Continued)

(51) Int. Cl.
*A24F 40/30* (2020.01)
*A24F 40/46* (2020.01)
(Continued)

(52) U.S. Cl.
CPC ............. *A24F 40/30* (2020.01); *A24F 40/10* (2020.01); *A24F 40/42* (2020.01); *A24F 40/44* (2020.01); *A24F 40/46* (2020.01); *A24F 40/48* (2020.01); *A24F 40/53* (2020.01); *A24F 40/57* (2020.01); *A61M 11/042* (2014.02); *A61M 2205/3368* (2013.01); *A61M 2205/3584* (2013.01); *A61M 2205/3653* (2013.01); *A61M 2205/587* (2013.01); *A61M 2205/8206* (2013.01)

(58) Field of Classification Search
CPC ...................................................... A24F 40/30
See application file for complete search history.

(56) References Cited

U.S. PATENT DOCUMENTS

2016/0353800 A1* 12/2016 Di Carlo ................. A24F 40/30
2017/0119058 A1* 5/2017 Cameron ............. A24B 15/167
(Continued)

FOREIGN PATENT DOCUMENTS

KR 20130001035 U * 2/2013

OTHER PUBLICATIONS

Nuleaf, "How Much THC is in CBD Oil?" Oct. 28, 2019, https://nuleafnaturals.com/how-much-thc-is-in-cbd-oil/ (Year: 2019).*

*Primary Examiner* — Cynthia Szewczyk
(74) *Attorney, Agent, or Firm* — Edmond A. DeFrank

(57) ABSTRACT

The embodiments disclose a method including creating a dual product vaporizer for use in vaping two different types of products at the same time, atomizing the two different types of products using two heaters for allowance of different burn temperatures for each of the two different types of products, wherein the two heaters are configured to operate at two different temperatures, wherein the two heaters are configured to operate at the same temperature, wherein the dual product vaporizer is configured to operate with only one product cartridge inserted, using at least one rechargeable battery to power the two heaters and an LED light battery indicator, and using two individual draw holes for drawing atomized product vapors from two individual product cartridges at the same time.

7 Claims, 7 Drawing Sheets

Related U.S. Application Data

(60) Provisional application No. 63/007,340, filed on Apr. 8, 2020.

(51) Int. Cl.
*A24F 40/48* (2020.01)
*A24F 40/42* (2020.01)
*A24F 40/44* (2020.01)
*A24F 40/53* (2020.01)
*A24F 40/10* (2020.01)
*A61M 11/04* (2006.01)
*A24F 40/57* (2020.01)

(56) References Cited

U.S. PATENT DOCUMENTS

| | | | |
|---|---|---|---|
| 2017/0182267 A1* | 6/2017 | Cameron | A61M 11/042 |
| 2017/0354180 A1* | 12/2017 | Fornarelli | H05B 3/04 |
| 2019/0124982 A1* | 5/2019 | Atkins | A24F 40/30 |
| 2020/0163382 A1* | 5/2020 | Trzecieski | A24F 40/46 |

* cited by examiner

DUAL PRODUCT VAPORIZER METHOD AND DEVICES

CROSS-REFERENCED TO RELATED APPLICATIONS

This Patent Application is a Continuation and claims priority to United States Patent Application entitled: "DUAL PRODUCT VAPORIZER METHOD AND DEVICES", U.S. Ser. No. 17/149,749 filed on Jan. 15, 2021 filed by Emma S. Glaser, the U.S. Patent Application being incorporated herein by reference and this application is based on U.S. Provisional Patent Application Ser. No. 63/007,340 filed Apr. 11, 2021, entitled "DUAL PRODUCT VAPORIZER METHOD AND DEVICES" by Emma S. Glaser.

BACKGROUND

Vaping has gained popularity. Current vaping devices provide for one product type to be inserted at a time. Many who vape enjoy vaping two different products. Those who prefer to vape two products generally buy two atomizers, one for one product type and the second for a different product type. This drives up their cost. Some who vape prefer to enjoy the two products of their choice at the same time. This becomes difficult with two devices.

DETAILED DESCRIPTION OF THE INVENTION

In the following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview

It should be noted that the descriptions that follow, for example, in terms of a dual product vaporizer method and devices are described for illustrative purposes and the underlying system can apply to any number and multiple types of vaping products. In one embodiment of the present invention, the dual product vaporizer method and devices can be configured using two draw holes. The dual product vaporizer method and devices can be configured to include two heaters and can be configured to include two vaping product cartridges using the present invention.

Dual Product Vaporizer Method and Devices

Figure 1:
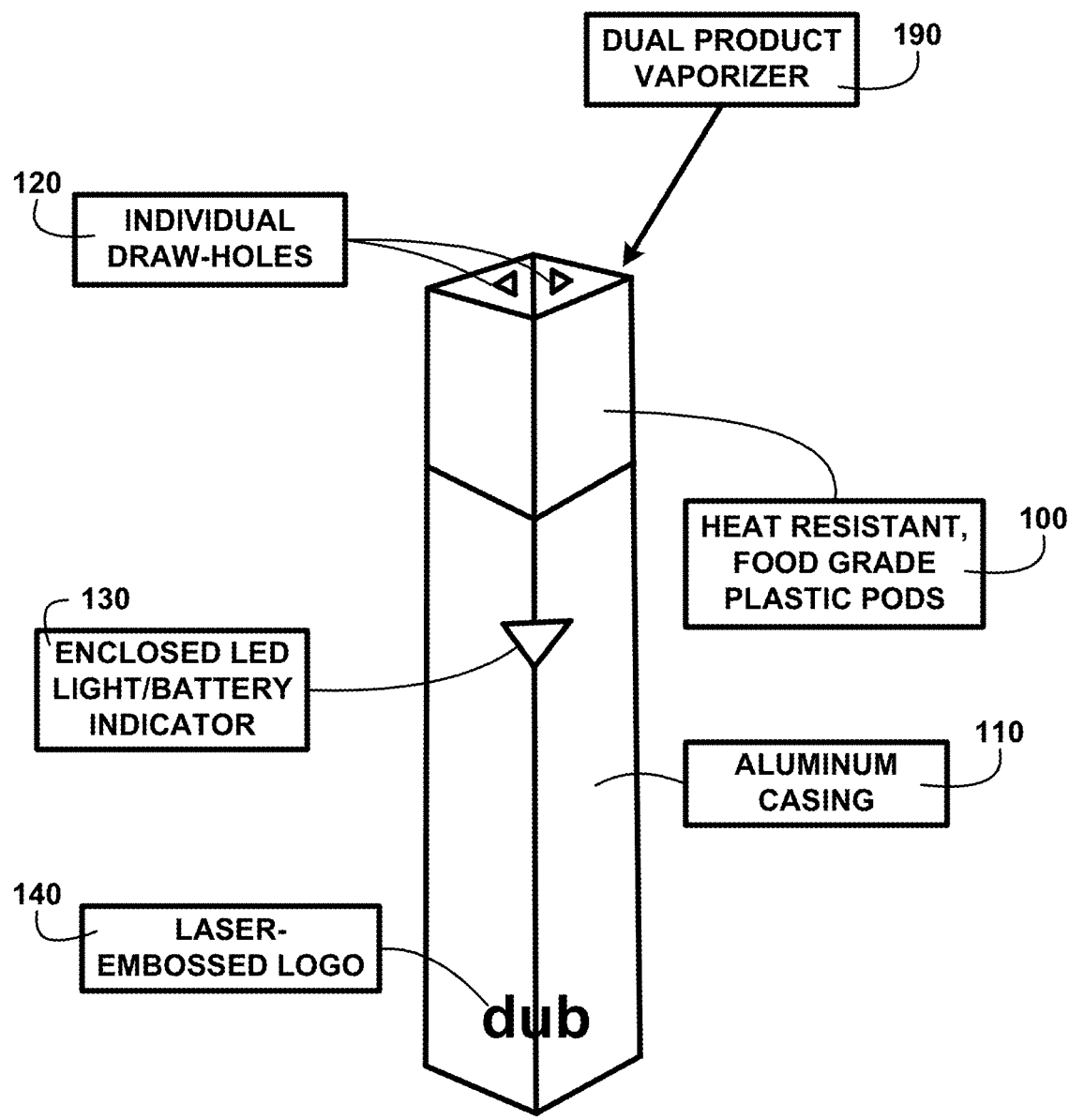
FIG. 1 shows for illustrative purposes only an example of a dual product vaporizer method and devices of one embodiment.

FIG. 1 shows for illustrative purposes only an example of a dual product vaporizer method and devices of one embodiment. FIG. 1 shows a dual product vaporizer 190 for use in vaping two different types of products at the same time. The dual product vaporizer 190 is convenient for those people vaping nicotine and THC/CBD. A user can combine vaping both nicotine and THC simultaneously. In another embodiment a user can combine vaping both nicotine and CBD simultaneously. This is appealing as it is common for THC vape users to also vape nicotine. The THC vaping industry is expanding as more states legalize recreational cannabis, and nicotine vapes are in demand as well.

The dual product vaporizers are heat resistant, food grade plastic pods 100 of one section where the user draws the atomized products. The balance of the housing is an aluminum casing 110. One terminus includes individual drawholes 120 for each of the different products. An enclosed LED light/battery indicator 130 located on the interior projects light through the heat resistant, food grade plastic pods 100 to keep the user aware of the battery charge remaining on the dual product vaporizer 190. A laser-embossed logo 140 identifies the dual product vaporizer 190 brand so users can more readily find the product of one embodiment.

Internal Elements of the Dual Product Vaporizer

Figure 2:
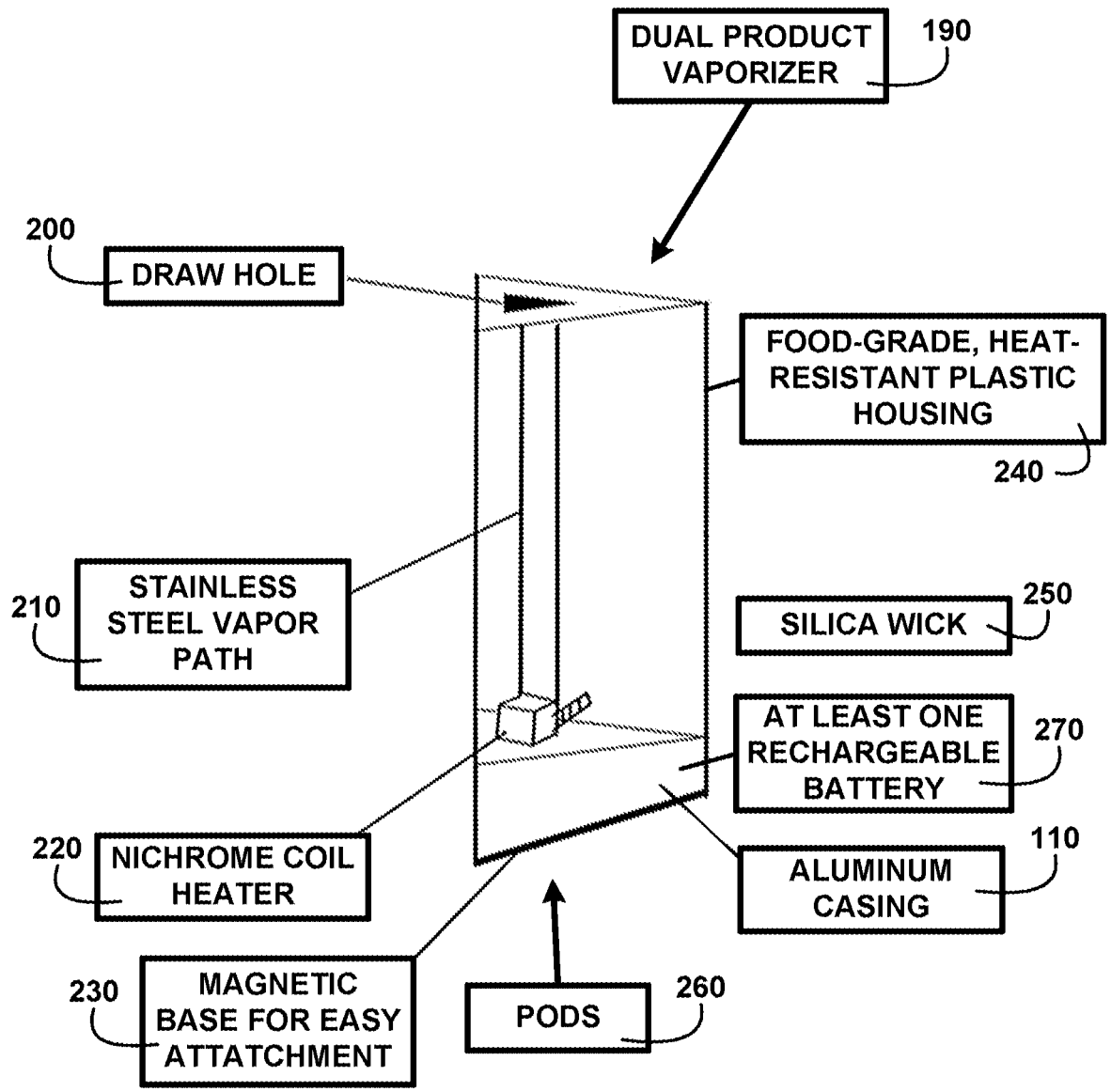
FIG. 2 shows for illustrative purposes only an example of a transparent view of the internal elements of the dual product vaporizer of one embodiment.

FIG. 2 shows for illustrative purposes only an example of a transparent view of the internal elements of the dual product vaporizer of one embodiment. FIG. 2 shows the interior of the dual product vaporizer 190 where the plastic and aluminum housing is transparent so the interior elements are visible. A draw hole 200 is showing at one end of a stainless steel vapor path 210. At the opposite end of the stainless steel vapor path 210 is a nichrome coil heater 220.

The nichrome coil heater 220 powered by the battery is used to atomize a product. The nichrome coil heater 220 in one embodiment includes a wireless digital thermostat 221 allowing a user to change the nichrome coil heater 220 temperature setting wirelessly using a dual product vaporizer app for transmitting to the wireless digital thermostat 221 the user's temperature change setting. A magnetic base for easy attachment 230 is positioned at the end of the dual product vaporizer 190 opposite to the draw hole. The food-grade, heat-resistant plastic housing 240 is shown in a transparent illustration. A silica wick 250 is inserted into a product cartridge to heat the product from the nichrome coil heater 220. The elements of the dual product vaporizer 190 shown are a part of the pods 260 that make up the dual product vaporizer 190 in one embodiment.

The dual product vaporizer 190 combines in one embodiment both THC and nicotine into one vaporized hit. The dual product vaporizer 190 includes at least one rechargeable battery 270 and two separate cartridges to be used in combination. Each user will be able to choose the amount of nicotine they desire, and the strain of THC they prefer. In one embodiment a first at least one rechargeable battery 270 will automatically power two temperature settings. In another embodiment a second at least one rechargeable battery 270 includes sensors that determine the distillate to be atomized. The second at least one rechargeable battery 270 includes a digital processor and digital memory device to determine and adjust temperature settings to automatically provide power to the nichrome coil heater 220 to the atomizer to reach a predetermined temperature for the determined distillate.

It is common for a THC vape user to vape nicotine as well, about 70%. In another embodiment the dual product vaporizer 190 can also provide CBD cartridges for those who do not enjoy the effects of THC. The user can elect to vape only one product for example one from the group of THC, Nicotine, or CBD independently. The liquid products for the cartridges will include nicotine liquid and premium quality THC/CBD distillates. The vaporizer includes two separate atomizers, one for nicotine and a second atomizer for THC/CBD since they burn at different temperatures. The cartridges for nicotine and THC/CBD will be independent, but fit flush to each other with the use of a magnet. The vaporizer is configured to operate both heating atomizers independently with only one cartridge inserted for either heating atomizer. In another embodiment the vaporizer is configured to house two heating atomizers that operate at the same temperature to accommodate for example two cartridges for THC/CBD of one embodiment.

The use and sale of THC is regulated and each state has different licensing regulations. Some states permit and have legalized within that state the use of THC cannabis for medical and recreational use. Other states have legalized the use of THC cannabis for medical purposes only but not recreational use. In yet other states they have not legalized the use of THC cannabis for any purpose. CBD has been legalized by the federal government if it's derived from hemp plants and if it has less than 0.3% THC. Therefore the provision and sale of THC and CBD cartridges for the dual product vaporizer 190 will abide by the Federal and individual state laws.

USB-C Charging Port

Figure 3:
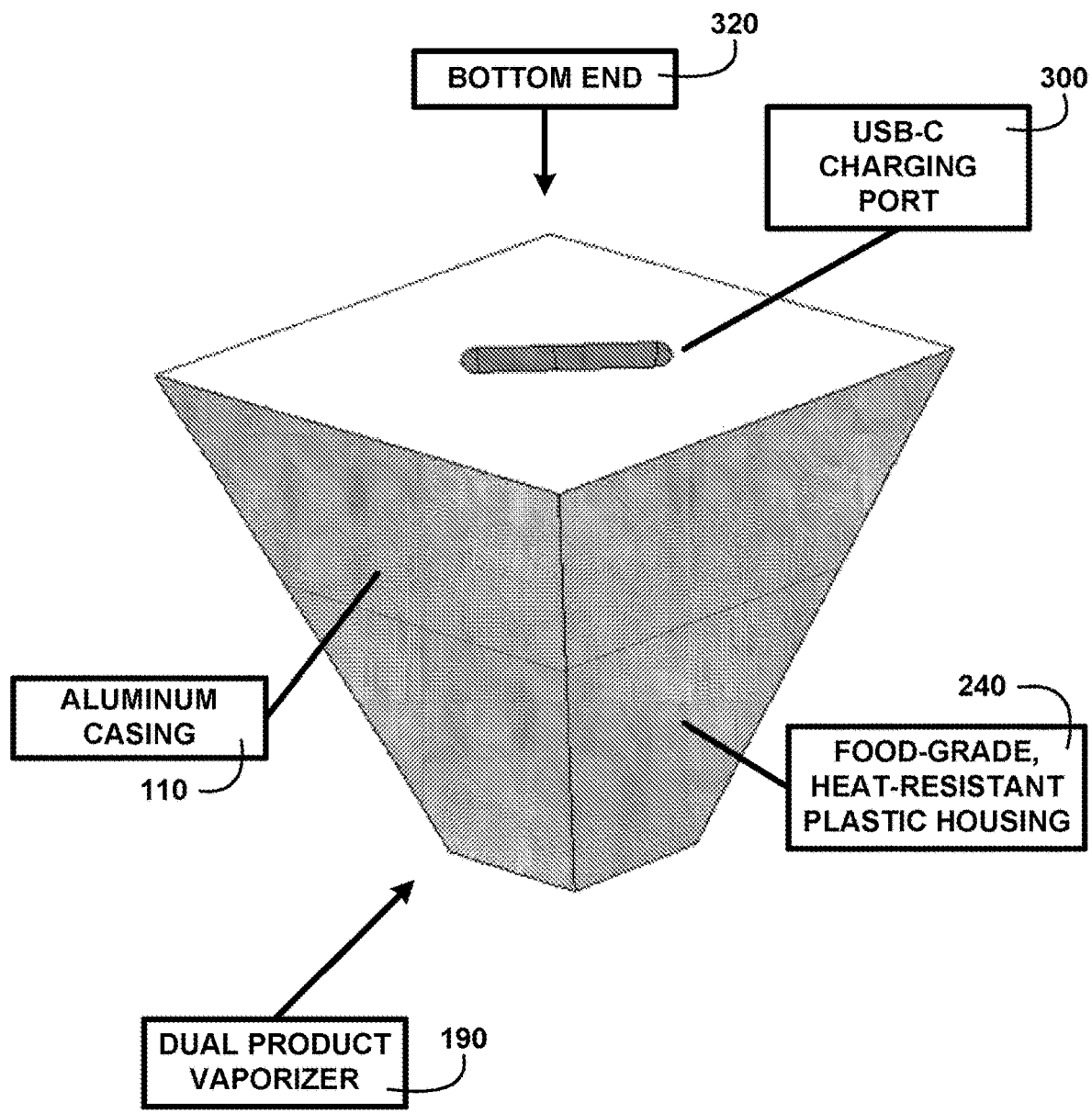
FIG. 3 shows for illustrative purposes only an example of a USB-C charging port of one embodiment.

FIG. 3 shows for illustrative purposes only an example of a USB-C charging port of one embodiment. FIG. 3 shows the food-grade, heat-resistant plastic housing 240 and the dual product vaporizer 190 USB-C charging port 300 located at the bottom end 320 of the aluminum casing 110 of FIG. 1. The USB-C charging port 300 is used to plug in a USB-C plug from a DC transformer of one embodiment.

Front View of the Dual Product Vaporizer

Figure 4A:
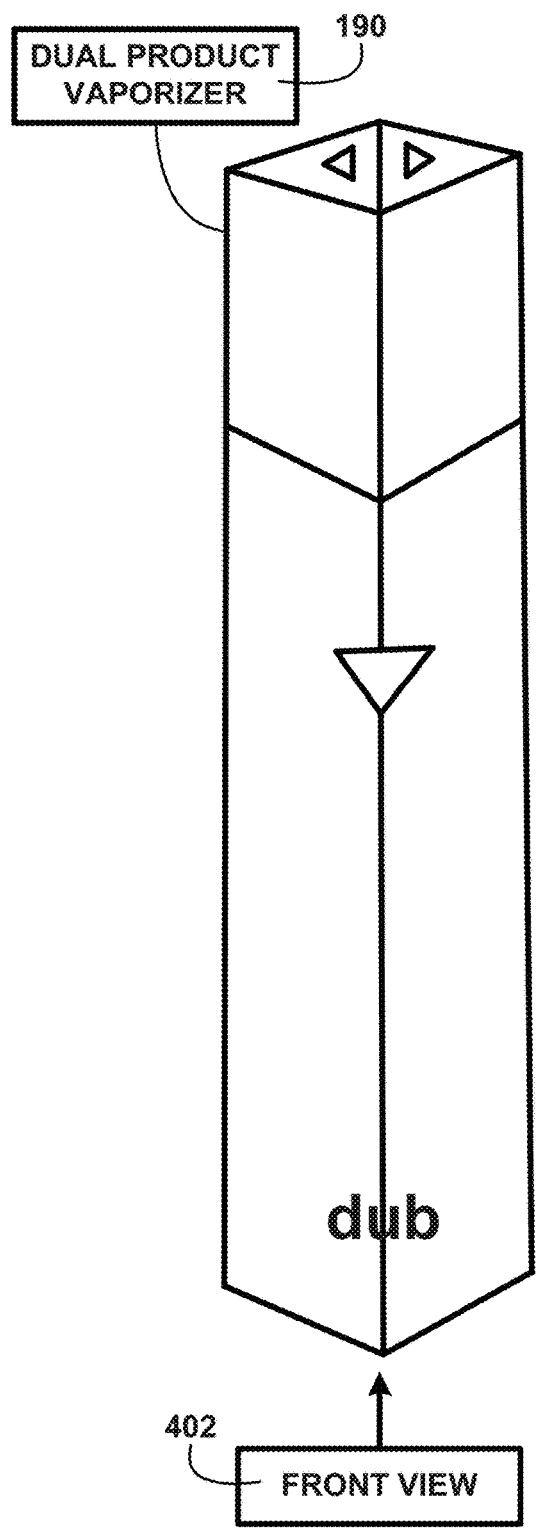
FIG. 4A shows for illustrative purposes only an example of a front view of the dual product vaporizer of one embodiment.

FIG. 4A shows for illustrative purposes only an example of a front view of the dual product vaporizer of one embodiment. FIG. 4A shows a front view 402 of the dual product vaporizer 190. The front view 402 shows the length of the front is longer than the front to back length of one embodiment.

Side View of the Dual Product Vaporizer

Figure 4B:
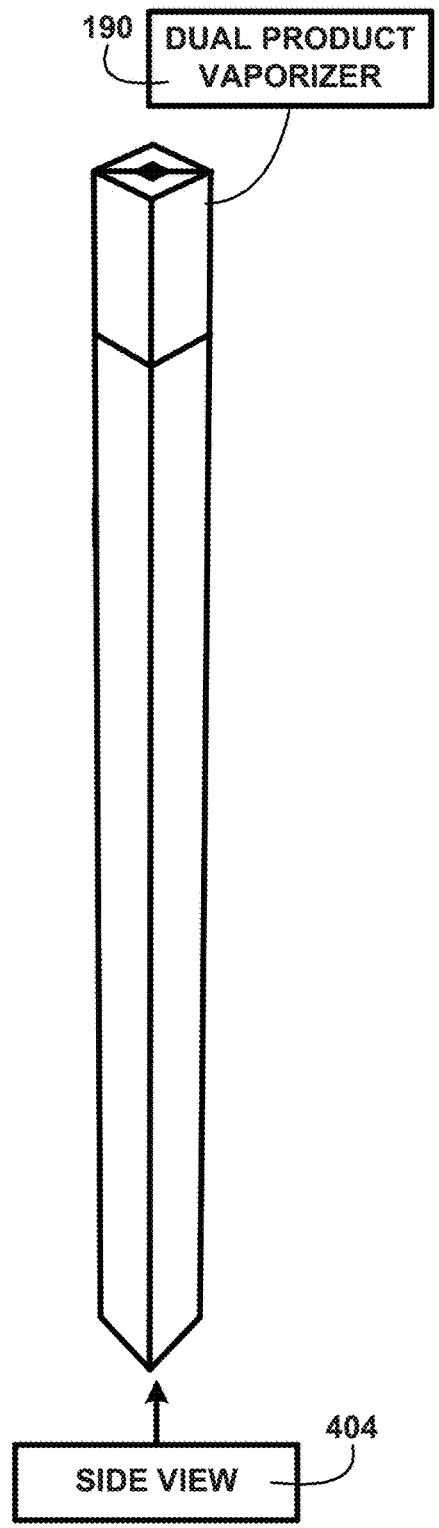
FIG. 4B shows for illustrative purposes only an example of a side view of the dual product vaporizer of one embodiment.

FIG. 4B shows for illustrative purposes only an example of a side view of the dual product vaporizer of one embodiment. FIG. 4B shows a side view 404 of the dual product vaporizer 190. The side view 404 shows the length of the front to back to be shorter than the side to side length of one embodiment.

Push Button Controls

Figure 5A:
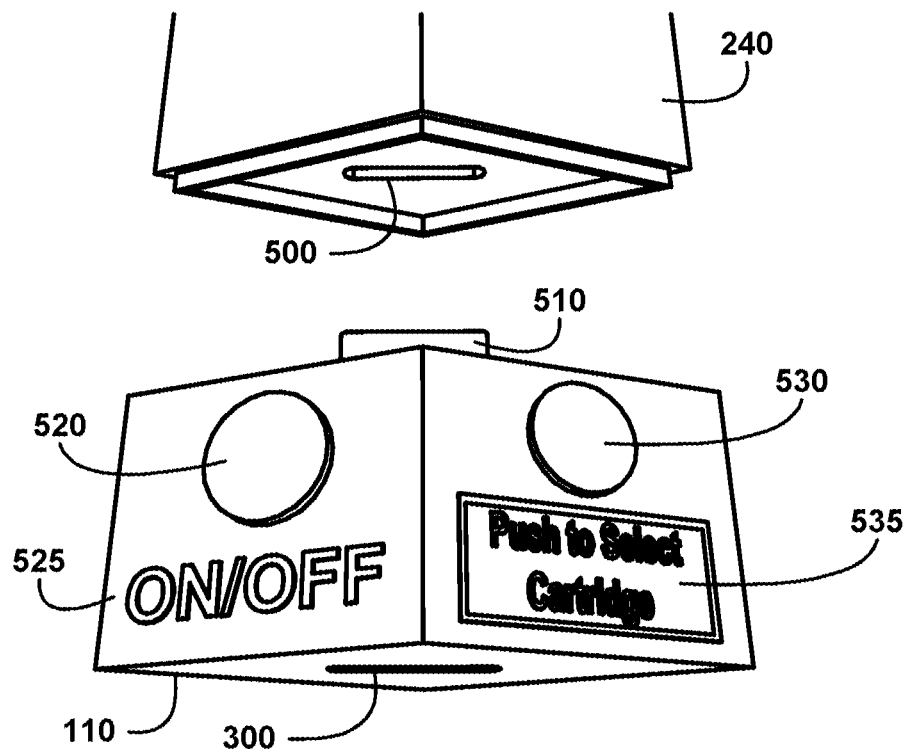
FIG. 5A shows for illustrative purposes only an example of push button controls of one embodiment.

FIG. 5A shows for illustrative purposes only an example of push button controls of one embodiment. FIG. 5A shows the food-grade, heat-resistant plastic housing 240 in a bottom view. The food-grade, heat-resistant plastic housing 240 in a bottom view reveals a nichrome coil heater power inlet 500. A nichrome coil heater power plug 510 coupled to a battery inserts into the nichrome coil heater power inlet 500 to provide power to the nichrome coil heater 220 of FIG. 2. An on/off push button control 520 identified with an on/off push button label 525 includes an LED light (not shown) that illuminates the on/off push button control 520 so the user is aware the power is on. A cartridge selection push button 530 is available to be used the user with a push to select cartridge instruction label 535 and cycles through a list of cartridges until the user sees the cartridge installed In the dual product vaporizer 190 of FIG. 1. The buttons are coupled to the aluminum casing 110 that also houses the USB-C charging port 300.

In another embodiment the cartridge selection push button 530 automatically displaying the cartridge installed in the dual product vaporizer 190 of FIG. 1 when installed.

Setting Cartridge Selected for Nicotine

Figure 5B:
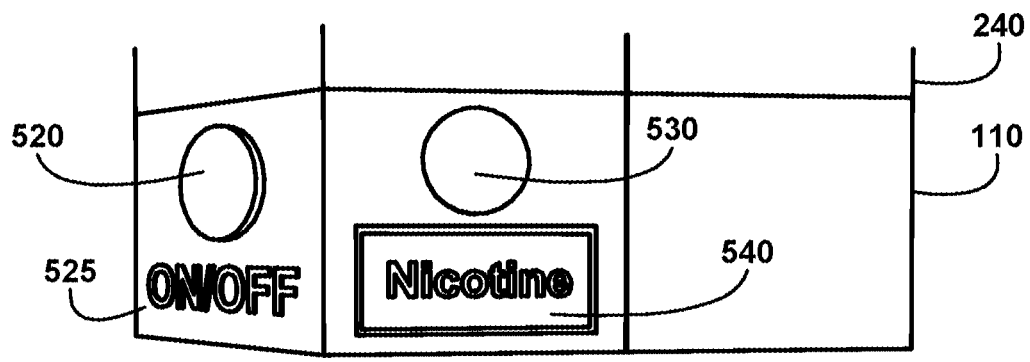
FIG. 5B shows for illustrative purposes only an example of setting cartridge selected for nicotine of one embodiment.

FIG. 5B shows for illustrative purposes only an example of setting cartridge selected for nicotine of one embodiment. FIG. 5B shows the food-grade, heat-resistant plastic housing 240, the aluminum casing 110, on/off push button control 520, on/off push button label 525 and cartridge selection push button 530. In this example the user has selected a cartridge with nicotine 540. The nicotine cartridge selected will remind the user of the cartridge installed in that dual product vaporizer 190 of FIG. 1 of one embodiment.

Setting Cartridge Selected for Hemp CBD<0.3 THC

Figure 5C:
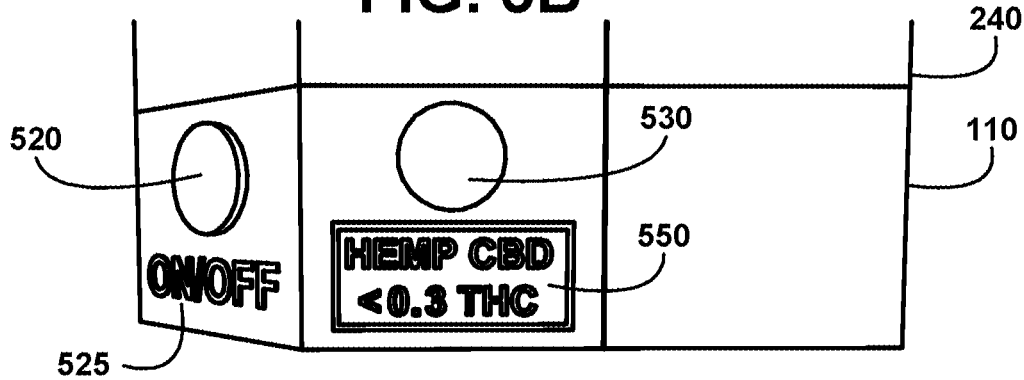
FIG. 5C shows for illustrative purposes only an example of setting cartridge selected for hemp CBD<0.3 THC of one embodiment.

FIG. 5C shows for illustrative purposes only an example of setting cartridge selected for hemp CBD<0.3 THC of one embodiment. FIG. 5C shows the food-grade, heat-resistant plastic housing 240, the aluminum casing 110, on/off push button control 520, on/off push button label 525 and cartridge selection push button 530. In this example the user has selected a cartridge with hemp CBD with less than 0.3 THC of one embodiment.

Dual Product Vaporizer Single Draw Hole Cap

Figure 6A:
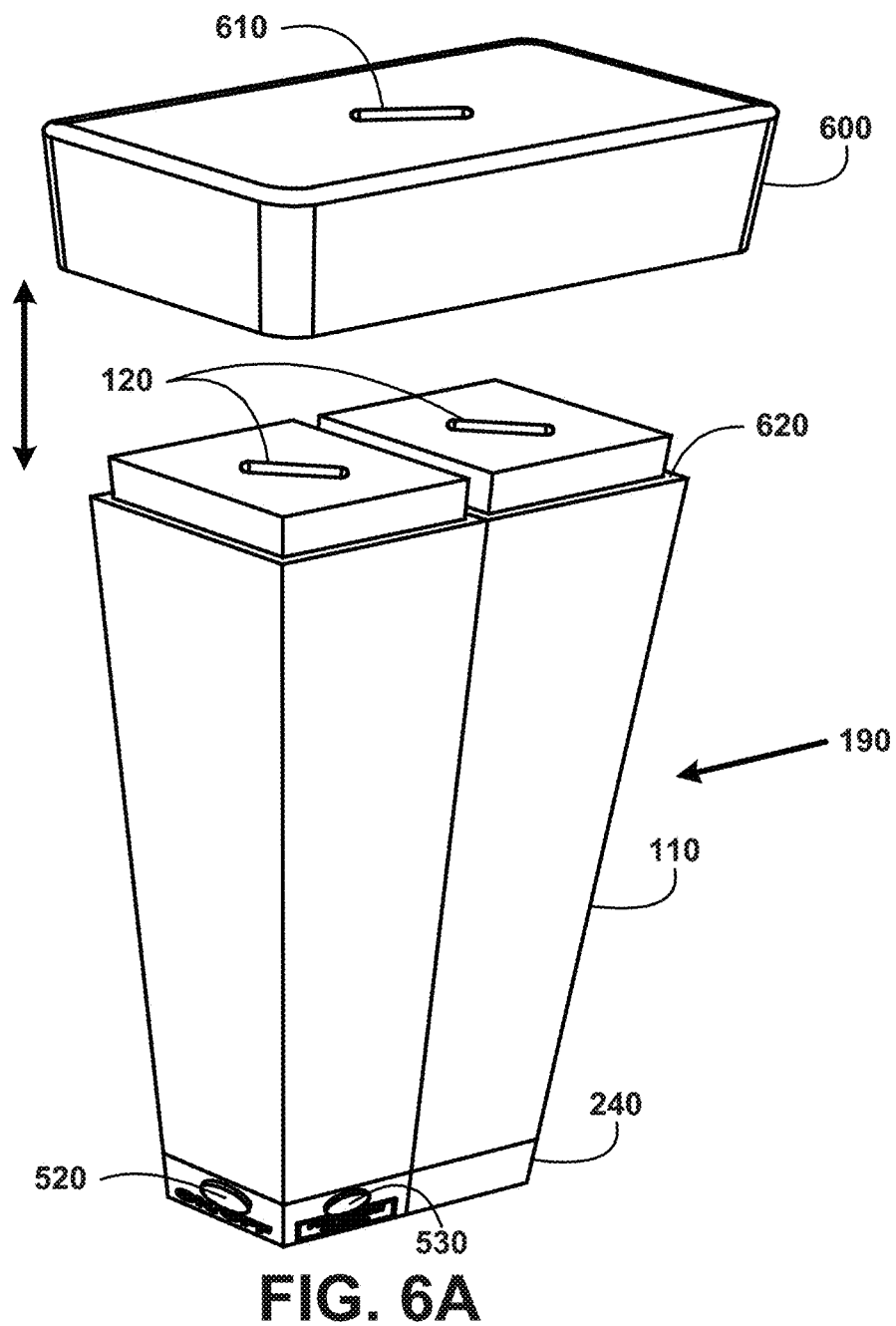
FIG. 6A shows for illustrative purposes only an example of a dual product vaporizer single draw hole cap of one embodiment.

FIG. 6A shows for illustrative purposes only an example of a dual product vaporizer single draw hole cap of one embodiment. FIG. 6A shows the food-grade, heat-resistant plastic housing 240, the aluminum casing 110, on/off push button control 520, and cartridge selection push button 530. The dual product vaporizer 190 in this example is shown with two vaporizers each with a draw hole the user can draw smoke from each dual product vaporizer 190 cartridge installed. The cartridge includes a cap stopping ledge 620. When a single draw hole cap 600 is installed the cap stopping ledge 620 prevents the single draw hole cap 600 from touching the cartridge draw holes and leaves a gap below the single draw hole cap 600 single draw hole 610 whereby the user can draw from both cartridges simultaneously with a balanced draw from each cartridge of one embodiment.

Single Draw Hole Cap Mounting Ledge

Figure 6B:
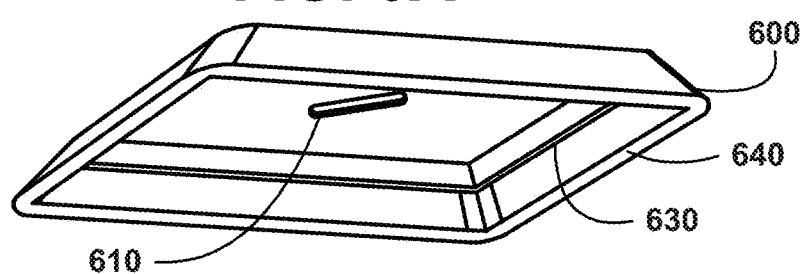
FIG. 6B shows for illustrative purposes only an example of a single draw hole cap mounting ledge of one embodiment.

FIG. 6B shows for illustrative purposes only an example of a single draw hole cap mounting ledge of one embodiment. FIG. 6B shows an interior view of the single draw hole cap 600 including the single draw hole 610. Also seen is an interior complementary stopping ledge 630 which rests on the cap stopping ledge 620 when the cap is installed by the user. A single draw hole cap apron 640 rests below the cartridge top edge and prevents drawn smoke from escaping of one embodiment.

Dual Product Vaporizer App

Figure 7:
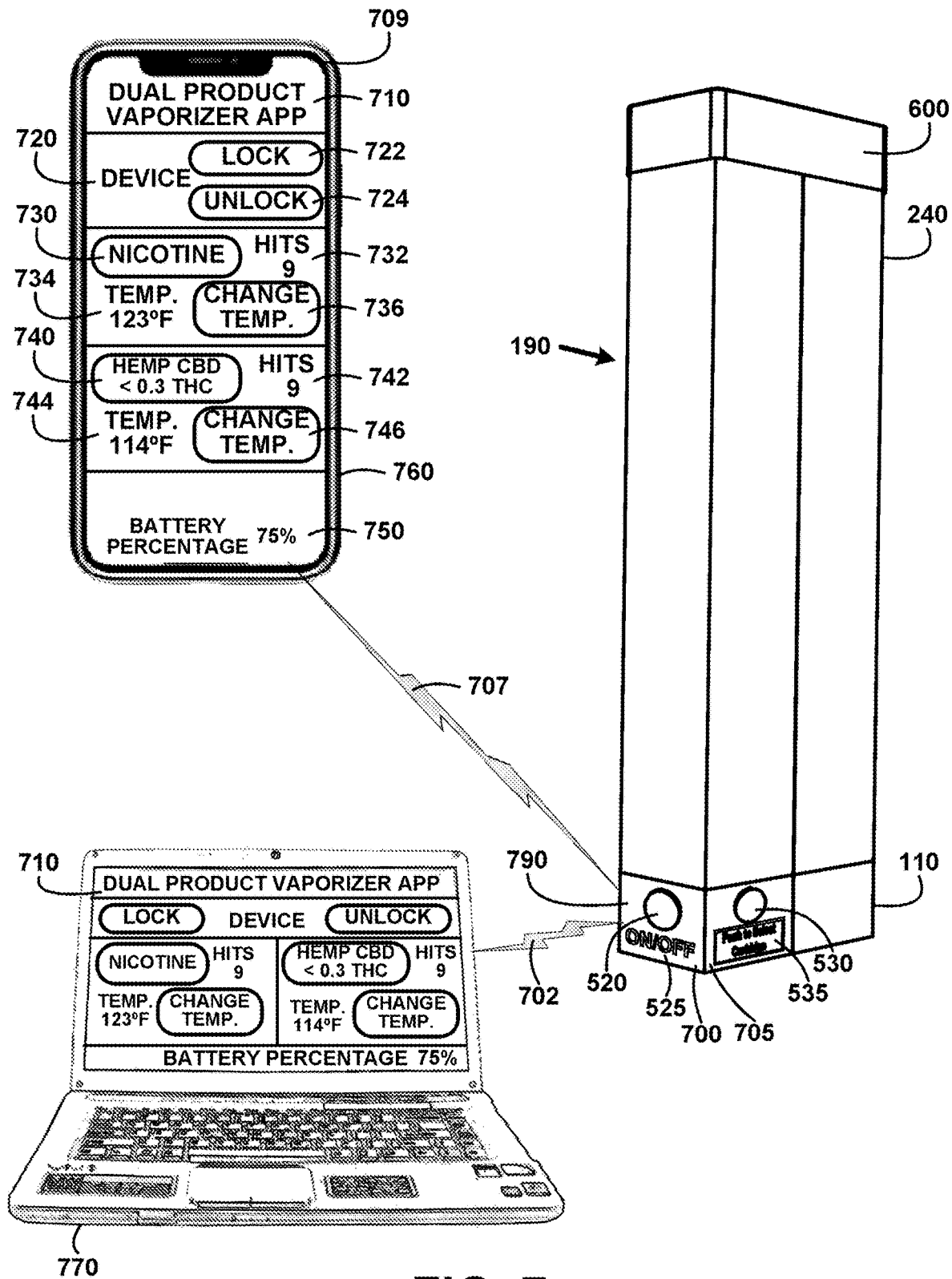
FIG. 7 shows for illustrative purposes only an example of a dual product vaporizer app of one embodiment.

FIG. 7 shows for illustrative purposes only an example of a dual product vaporizer app of one embodiment. FIG. 7 shows the single draw hole cap 600, the food-grade, heat-resistant plastic housing 240, the aluminum casing 110, on/off push button control 520, on/off push button label 525, cartridge selection push button 530 and select cartridge instruction label 535. Also housed inside the aluminum casing 110 and not showing are a WI-FI communication device 700 and a cellular communication device 705 for receiving and transmitting data from each of the two cartridges. In one instance the WI-FI communication device 700 is transmitting and receiving data via WI-FI to a user laptop computer 770 with a dual product vaporizer app 710.

In a second instance the cellular communication device 705 is transmitting and receiving data via cellular communication 707 to a user with the dual product vaporizer app 710 installed on a user smart phone 709 or other digital device. The user may prevent someone else from using the dual product vaporizer 190 with the dual product vaporizer app 710 device 720 elements that includes a lock 722 and unlock 724 feature. Pressing the lock 722 button instructs the dual product vaporizer 190 to open a digital circuit breaker to disconnect power from the atomizer. Pressing the unlock 724 button transmits a signal to close the digital circuit breaker to restore power to the atomizer. The digital circuit breaker is embedded into the on/off push button control 520. The dual product vaporizer app 710 displays the status of a first cartridge with nicotine 730. The first cartridge using a digital processor and a digital memory device tracks a user's draws on the dual product vaporizer 190 and transmits that data to the dual product vaporizer app 710 where it displays the user hits 9 732. The first cartridge with nicotine 730 also transmits to the user smart phone 709 the temp. 123° F. 734 setting for the atomizer. The user may press the change temp. 736 button of the dual product vaporizer app 710 to adjust in this instance to increase with a higher temperature or decrease with a lower temperature the amount of nicotine 730 being atomized.

The second cartridge using a digital processor and a digital memory device tracks a user's draws on the dual product vaporizer 190 and transmits that data to the dual product vaporizer app 710 where it displays the user hits 9 742. The user hits are the same as reported by the first cartridge with the single draw hole cap 600 of FIG. 6A as the user draws on both cartridge are simultaneously occurring.

The second cartridge with hemp CBD<0.3 THC 740 also transmits to the user smart phone 709 the temp. 114° F. 744 setting for the hemp CBD<0.3 THC 740 second cartridge atomizer. The user may press the change temp. 746 button of the dual product vaporizer app 710 to adjust in this instance to increase with a higher temperature or decrease with a lower temperature the amount of hemp CBD<0.3 THC 740 being atomized. The nichrome coil heater 220 of FIG. 2 in one embodiment includes a wireless digital thermostat 221 of FIG. 2 allowing the user to change the nichrome coil heater 220 of FIG. 2 temperature setting wirelessly using the dual product vaporizer app 710 for transmitting to the wireless digital thermostat 221 of FIG. 2 the user's temperature change setting.

The cartridges also transmits Bluetooth 760 signals to the user smart phone 709 where the signals include audio data for the user to listen to the status reports from the cartridges. Additionally the cartridges transmit a battery percentage 75% 750 for display on the dual product vaporizer app 710 to alert the user when the battery may need recharging of one embodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A vaping system, comprising:
at least one cartridge having a draw hole at a proximal end and a base at a distal end;
at least a first and a second atomizer coupled to the at least one cartridge;
at least one battery coupled to the at least one cartridge base and configured to provide power to the at least first and second atomizers;
a switch coupled to the at least first and second atomizers having a first setting configured to power the first atomizer independently from the second atomizer and a second setting configured to power the second atomizer independently from the first atomizer and a third setting configured to power the first and second atomizers simultaneously;
at least one bundle of fibers coupled to each of the at least a first and a second atomizer configured to heat a vaping substance from a heater;
a first compartment located within the at least one cartridge and configured to receive a first vaping substance;
a second compartment located proximate to the first compartment and configured to receive a second vaping substance; and
wherein the at least a first and a second atomizer are configured to heat the first vaping substance at a first temperature and heat the second vaping substance at a second different temperature; and
wherein the draw hole is configured to allow a user to vape the first vaping substance independently from the second vaping substance when the first setting is activated and to vape the second vaping substance independently from the first vaping substance when the second setting is activated and to vape the first and second vaping substances simultaneously when the third setting is activated.

2. The vaping system of claim 1, wherein the at least one bundle of fibers coupled to an atomizer is configured to heat a vaping substance from a nichrome coil heater powered with the at least one battery.

3. The vaping system of claim 1, wherein the cartridge is made with materials including heat resistant, food grade plastic pods for one section for a user drawing atomized vaping substances and housed in an aluminum casing.

4. The vaping system of claim 1, wherein the first vaping substance is nicotine and the second vaping substance is THC/CBD.

5. The vaping system of claim 1, further comprising a plurality of sensors coupled to each atomizer configured to transmit and receive data from the plurality of sensors to a user smart phone with a vaping application.

6. The vaping system of claim 1, wherein the at least one battery is a rechargeable battery.

7. The vaping system of claim 1, further comprising a WI-FI communication device coupled to the battery and configured to communicate with an electronic device.

* * * * *